United States Patent [19]

Schechter

[11] 4,120,649

[45] Oct. 17, 1978

[54] TRANSPLANTS

[76] Inventor: Israel Schechter, Neve Matz 12, Rehovoth, Israel

[21] Appl. No.: 671,728

[22] Filed: Mar. 29, 1976

[30] Foreign Application Priority Data

Apr. 10, 1975 [IL] Israel .................................. 47062

[51] Int. Cl.$^2$ ........................... C14C 3/16; A61F 1/24
[52] U.S. Cl. ............................................ 8/94.11; 3/1; 3/1.3; 3/1.4; 3/1.5; 128/1 R
[58] Field of Search ................... 8/94.11; 3/1, 1.3, 1.4, 3/1.5; 128/1

[56] References Cited

U.S. PATENT DOCUMENTS

| | | | |
|---|---|---|---|
| 3,057,775 | 10/1962 | Rendon | .................................. 424/75 |
| 3,974,526 | 8/1976 | Dardik et al. | ............................. 3/1.4 |
| 3,988,782 | 11/1976 | Dardick et al. | ............................... 3/1 |

OTHER PUBLICATIONS

Proc. Nat. Acad. Sci., USA, vol. 68, No. 7, pp. 1590–1593, Jul. 1971; Schechter.
Rosenberg, Management of Arterial Occlusive Disease, p. 169, 1971.
Snyder et al., Amer. Journal of Hospital Pharmacy, vol. 22, Jun. 1963, pp. 321–327.

*Primary Examiner*—John Kight, III
*Attorney, Agent, or Firm*—Browdy and Neimark

[57] ABSTRACT

Transplants, particularly from pigskin, from humans, and amniotic membranes of newborns are prepared from the appropriate tissue — which tissue is treated with the compound glutaraldehyde (GA).

The so treated tissue excels by favorable biological function: increased resistance to infection, markedly reduced antigenicity, and prolonged retention time on the recipient, as well as the possibility to store so treated tissue for a prolonged span of time.

25 Claims, 1 Drawing Figure

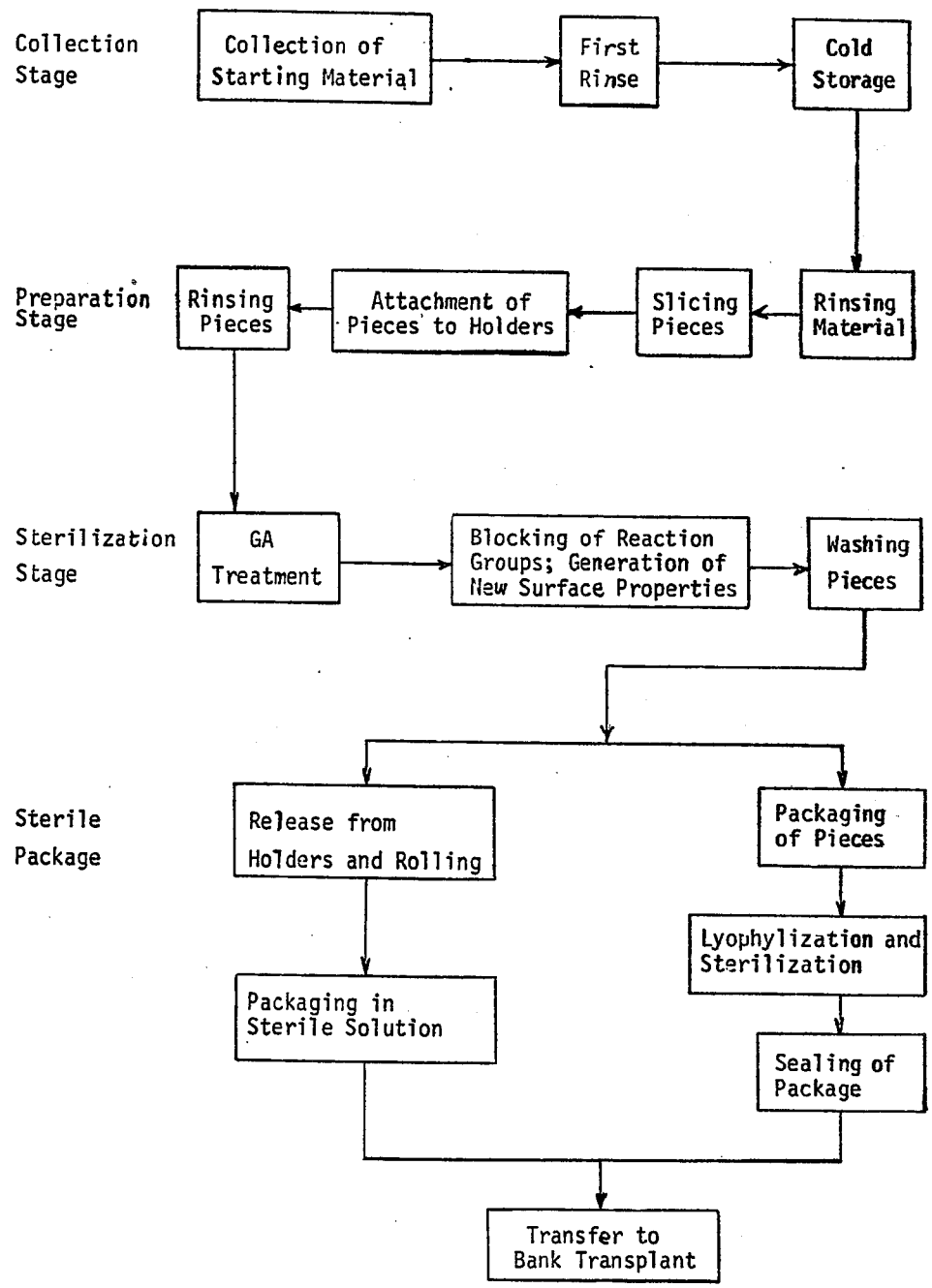
BLOCK DIAGRAM OF PROCESS

TRANSPLANTS

BACKGROUND OF INVENTION

The present invention relates to a process of preparing grafts for biological dressing, such as applied in the case of burns, wounds, ulcers, and removal of patches of skin in such a manner as to overcome histocompatibility barriers, and so as to make possible grafts which have a long, effective duration in the recipient, and which have increased resistance to infection and are substantially devoid of undesired effects on the recipient.

The main obstacle encountered in organ transplantation is the immune rejection of the transplant. The rejection phenomenon originates from antigenic differences between the cells of the recipient and the transplant, as well as from the natural immune response of the organism towards "non-self" antigens. Attempts to prolong the survival of allografts and xenografts, both in experimental models and in medical practice, have been mainly aimed at the supression of the immune apparatus of the recipient. This has been achieved by means of cytotoxic drugs, antimetabolites, corticosteroids and antilymphocytic serum. The generalized immunosuppression, however, is accompanied by undesirable toxic effects, decreased resistance to infection and reduction in the level of the haemopoietic stem cells. Another possibility is to attenuate, or to abolish completely, the antigenicity of the graft with preservation of its biological functions. The advantage of this approach is that the immune capacity of the recipient is not affected. Investigations along this line, have been, for the most part, unsuccessful. Most studies were performed with animals and only recently it has been subjected to clinical evaluation. Using laboratory animals, the treatment of allografts or xenografts in vitro, with cortisone, thalidomide or urethane prolonged their retention time by a factor of about two. The amount of drug locally applied to the skin was smaller than the amount required to achieve a similar effect by injecting the drug systemically. In attempts to modify the antigenic properties of grafts, the donor skin has been treated in vitro with streptokinase/streptodornase, or with RNA and DNA preparations of the recipient. Allograft survival was not prolonged by exposure of donor skin to transplantation antigens of the recipient. Minimal immune reaction was observed towards grafts in which cellular viability was destroyed in vitro treatment with formalin or cyanide or by freeze-drying. The majority of the dead grafts were retained by the host for a limited period of time.

Blood vessel xenografts treated by 1% solution of the enzyme ficin, then treated by 1.3% solution of dialdehyde starch for 18 hours, and stored in a solution containing 50% ethanol and 1% propylene oxide for sterility, were tested in experimental animals, and have been recently used clinically to replace damaged blood vessels. In the last few years freeze dried pig-skin xenografts have been used as temporary dressing in the treatment of burns. These dressings exhibit minimal or no antigenicity, but it is necessary to replace the freeze dried pig-skin dressing every 2-4 days before they become adherent and infected.

OBJECTS OF THE INVENTION

It is an object of the present invention to provide a process of treatment which will be favorable for the biological function of the graft, and which will render such graft resistant to infection. The increased resistance to infection and other properties, makes it possible to establish a "bank", where large quantities of treated tissues can be stored for long periods of time without significant loss of their efficacy when applied subsequently to patients. The process developed is applicable with equal efficiency for both allografts and xenografts. The use of xenografts overcomes the difficulties encountered by the limited supply of tissue from humans. The invention further relates to such pretreated tissues, to be used for grafts. Other and further features of the present invention will become apparent hereinafter.

SHORT SUMMARY OF THE INVENTION

The present invention is based on the hypothesis that if allografts or xenografts are treated in vitro with certain chemical reagents, the reacting groups might be directly and covalently bound to the histocompatibility antigen molecules, or in their close vicinity. In consequence, the histocompatibility antigens might be masked and become inaccessible to the immune apparatus of the recipient. The purpose of this approach is to achieve functional elimination of the antigens responsible for tissue rejection. A large number of chemical reagents can react under physiological conditions with functional groups present in tissue constituents. The extent and nature of the masking effect might be controlled by choosing the appropriate reagent. Moreover, chemically inert molecules can also be bound to tissues by means of bifunctional reagents. Another feature inherent in this approach is the capacity to generate new properties (say, positive or negative charges, hydrophobic groups, etc.) on the surface of the transplant. It seems possible that a particular treatment leading to a new contact surface in the transplant might favor its acceptance by the host, and favor its physiological functioning. After screening several chemicals, we selected for detailed studies and compound glutaraldehyde (GA) which is a bifunctional reagent capable of cross-linking proteins rapidly and effectively.

Also, the GA causes cross-linking of the proteins in the tissue. Consequently, the cross-linked protein exhibit increased resistance to proteolytic cleavage since they can hardly be unfolded. A major process by which bacteria destroy tissues is the result of their enzymic activity. Since unfolding of the protein substrate facilitate enzymes hydrolysis, we assumed and indeed found that the GA treated skin exhibits increased resistance to infection. This is an important property in the treatment of wounds since most of them are infected.

The process according to the present invention comprises a straight-forward treatment (without any preceeding enzymatic pretreatment) of the tissue such as skin, with a solution of predetermined strength of glutaraldehyde. It has been found that solutions of from 0.3% to 1% by weight glutaraldehyde in a 0.1% sodium bicarbonate or in 0.01M pH 7.3 phosphate buffer — 0.15M sodium chloride (PBS) were suitable. Suitable values of pH are in a wide range. It was possible to treat the tissues with GA at a pH of from about 4 to 12. A preferred range is about 6.5 to 9. The tissue was maintained in the solution for 7 to 20 minutes, and prior to the use, the tissue was freed from excess of glutaraldehyde by washing with the PBS solution or with sodium bicarbonate solution containing amino-acids or other appropriate reagents so as to block any residual reactive groups of the GA, and to modify the surface properties of the tissue.

The advantages of glutaraldehyde (GA)-treated graft is that it is devoid of any detectable antigenicity, it exhibits increased resistance to infection, and that it is retained on the recipient for long periods of time. In experimental animals GA-treated skin allografts and xenografts were retained up to about 100 days (compared to 12.8 days of freeze dried pig skin) without any sign of infection. When used clinically for the treatment of burned patients, the GA-treated allografts were retained on the wound bed for 21.8 days. The increased resistance to infection of GA-treated grafts can be attributed to the fact that GA is a potent cross-linking agent. The GA reacts rapidly with the amino groups in the protein and the bonds formed are quite stable. Consequently, proteins in the GA-treated graft are cross-linked and "fixed". It is well known that proteolytic activity is considerably enhanced by unfolding of the protein substrate. The unfolding process should be markedly retarded in cross-linked proteins. It is conceivable, therefore, that the cross-linked proteins in the GA-treated graft should be less vulnerable to digestion and maceration by proteolytic enzymes released by bacteria or damaged tissue in infected wounds. This point is illustrated in the following experiment. Different bacteria (E. coli, staphylococci, pseudomonas) readily cause an overwhelming infection of skin soaked in a solution containing $10^2$ bacteria/ml. On the other hand, when skin treated in 1% GA is exposed to these bacteria, much more bacteria ($10^4$–$10^6$ bacteria/ml) are required to induce significant infection of the GA-treated skin. Also 1% GA-solution has a potent bactericidal activity on skin. Normal skin carries a heterogenous population of bacteria, as manifested by the fact that sterile growth media become infected by soaking into it normal skin. On the other hand, by this procedure, bacteria were undetectable on skin previously treated in 1% GA.

Practical Results with GA-treated Tissue (Examples)

Results obtained with glutaraldehyde-treated skin allografts and xenografts (from mice, rats, and guinea pigs) showed that they behave in the same way as judged from retention time, gross inspection, microscopic examination, and assays for graft antigenicity. The GA-treated grafts are retained for long periods of time (an increase by more than six-fold as compared to untreated grafts. See Table I). The results in the Table relate to skin grafts which were soaked in a solution containing 3 mg per ml of glutaraldehyde in PBS, kept at room temperature in this solution for 20 minutes, and after this washed four times in PBS so as to remove any free glutaraldehyde. The thus treated skin was applied to the recipient, covered with vaseline gauze, and with plaster of Paris, which were removed after ten days. The GA-treated grafts are tightly bound to the recipient. They are initially soft, but become progressively stiffer with minimal shrinkage in size, and remain free from infection. The histology shows that the grafts are non-viable and fixed by the GA, they are avascularized but the general structure of the skin (epidermis, adnexa, and dermis) is preserved for about 3 months. The antigenicity of the GA-treated allografts and xenografts is very poor, actually it is undetectable. They do not elicit the formation of cytotoxic antibodies, and animals sensitized by untreated allografts retain the GA-treated allografts similarly to normal unsensitized recipients. The lack of transplantation immunity is also indicated by the fact that GA-treated isografts behave and are rejected similarly to GA-treated allografts and xenografts (see Table I). Microscopic examinations suggest that the mechanism of rejection of GA-treated grafts is similar to that operating in the rejection of an inert foreign body.

Table I.

Prolonged retention of glutaraldehyde-treated skin grafts

| Group | Donor[a] | Recipient | Graft treatment | No. of animals | Retention time (days) Average | Range |
|---|---|---|---|---|---|---|
| Allografts | | | | | | |
| A | BA | C57 | none | 26 | 12.9 | (11– 16 ) |
|  |  |  | GA | 22 | >108 | (29–>135) |
| B | C57 | BA | none | 17 | 13.6 | (11– 17 ) |
|  |  |  | GA | 16 | > 63 | (37–>70 ) |
| C | BN | Le | none | 13 | 14.3 | (13– 16 ) |
|  |  |  | GA | 16 | > 91 | (55–>130) |
| Xenografts | | | | | | |
| D | C57 | Le | none | 17 | 10.5 | (10– 12 ) |
|  |  |  | GA | 19 | >106 | (55–>130) |
| E | GP | Le | none | 9 | 15.3 | (14– 18 ) |
|  |  |  | GA | 12 | >105 | (62–>130) |
| F | BN | C57 | none | 9 | 16.1 | (15– 18 ) |
|  |  |  | GA | 13 | > 82 | (28–>120) |
| Isografts | | | | | | |
| G | C57 | C57 | none | 12 | >130 | ( >130 ) |
|  |  |  | GA | 13 | >120 | (88–>130) |
| H | BA | BA | none | 11 | >130 | ( >130 ) |
|  |  |  | GA | 9 | >104 | (58–>130) |
| I | Le | Le | none | 7 | >130 | ( >130 ) |
|  |  |  | GA | 10 | >103 | (62–>130) |

[a]Abbreviation for animals are: BA, BALB/c mice; C57, C57BL/6 mice; BN, Brown Norway rats; Le, Lewis rats; GP, guinea pigs of the N13 strain.
The symbol ">" indicates the last time of inspection when skin grafts were still retained on the recipient.

It is very impressive that the GA-treated skins remained free from infection throughout the long period of observation. This can probably be attributed to the cross-linking of the skin constituents by GA. It is well known that proteases degrade more rapidly unfolded proteins as compared to cross-linked proteins which remained frozen in the folded stage. To explore this further, there was tested the susceptibility of GA-treated skins to infestation by bacteria. The results show that GA kills bacteria commonly present on skin. Furthermore, when exposed to increasing concentrations of different bacteria (e.g. staphylococci, pseudomonas), the bacterial concentration required to initiate minor infestations of GA-treated skins is 10,000-fold higher than the concentration capable of inducing massive infestation of untreated skins.

The GA-treated graft is non-viable, yet not all dead grafts are alike. The retention of freeze-dried grafts was extended from 10 to 13 days. No extension was observed in cyanide-treated allografts and they shrank more rapidly than viable untreated allografts. On the other hand, with GA-treated grafts the retention time was much more prolonged (Table I) with minimal diminution in size.

The possibility of storing the GA-treated tissue for long periods of time without significant loss of their efficacy was brought out by the histological features of the treated graft and by the fact that GA sterilized the skin and that the treated graft exhibits increased resistance to infections. Indeed, GA-treated tissues, kept for six weeks, were used after this period with success. This suggests the feasibility of establishing a "bank" of GA-treated tissues, for subsequent use.

The marked prolongation in retention time and the properties of the GA-treated skins prompted us to evaluate the clinical use of GA-treated skin grafts as non-viable wound cover. The study included twenty-one patients with 15–50% burns of the total body surface. Each patient received GA-treated and untreated cadaver skin allografts. The average retention time of the GA-treated grafts was significantly increased — it was 21.8 days as compared to 10.9 days for the untreated grafts. Following the application of the GA-treated allografts, even after one month, the recipient site was found to be healthy and there was a good take of autograft in every case. Toxic effects were not observed in any of the patients as judged from clinical manifestations, and differential blood counts. Overt eosinophilia was not detected, indicating the lack of allergic reaction.

In the application of grafts with human patients the GA-treated skin was treated with alanin as a precautionary measure so as to avoid any possible free functional groups of GA. This is an optional step, and it is assumed that this is not necessary when the skin is washed thoroughly after the immersion in the GA solution.

As skin is one of the tissues having a very high antigenic component, the results indicate that the process according to the present invention will certainly give at least as good results with other tissues or organs, in which such problem of histocompatibility is less pronounced. Thus it is clear that the process of pretreatment with glutaraldehyde is applicable also to other tissues such as amniotic tissue of a newborn or blood vessels to substitute damaged vessels. In the latter case, glutamic acid or aspartic acid or any other suitable dicarboxylic agent, will be coupled via the GA to the surface of the blood vessels to be used as transplants. Thus there can be generated a negatively charged surface, which is known to diminish blood clotting. It is known that blood clotting, leading to thrombus formation, with the obstruction of blood flow, is one of the common complications of transplants of blood vessels. This can be overcome to a large extent by this treatment.

Tubular organs, such as intestine, blood vessels, or esophagus, can be used to replace damaged portions of esophagus, blood vessels or bile duct. The advantageous points in these cases are that the GA-treated material exhibits a markedly increased resistance to infection (and this is a common complication in esophagus and bile duct transplants), and the fact that the GA-treated material is readily penetrated by fibrillar elements from the recipient. GA-treated skin can be used not only for burns, but also as a dressing to damaged intestine or to close certain defects such as diaphragmatic hernia.

The modification of the surface properties of the tissues is of course according to the intended use. Thus, for optimal functioning of the graft in the recipient, it is advantageous to modify the surface of the tissue so as to provide positively charged or negatively charged groups. This may be effected by means of a suitable amino-acid or polymers, or by means of the attachment of any physiologically acceptable source of charged functional groups.

The surface properties of the tissue can also be modified by rendering the surface hydrophobic or hydrophylic. This can be effected by coupling with phenylalanine for hydrophobic surfaces, or with serine and glutamic acid or lysine so as to render it hydrophylic. Various agents can be used for such modifications and these will be varied according to the desired properties of the tissue to be transplanted.

Preferred Method of Preparation of Material for Transplants

In a first step the material destined to be served for the preparation of grafts is collected from the donor and is rinsed in a sterile physiological saline solution and stored away in cold storage until further treatment.

The treating process is initiated by rinsing the collected material with sterile physiological saline solution. After rinsing, the material is cut into pieces of appropriate size and such pieces are fixed in holders to prevent the pieces from becoming folded during the subsequent treatment. These holders may be of a type which remain with the said pieces until actual use as a graft or such which are left on the pieces until these latter are packed when the holders are removed and can be used again. Finally, there might be employed holders which form part of the equipment for carrying out the treating process. At all events, and whatever holders are employed, after having been adjusted in the holders, the assembly of holder and skin patches is submitted to a further rinsing with physiological, sterile saline solution.

What is to be done now, has to be done under sterile conditions. The main step of the process would be to treat the cut pieces with glutaraldehyde solution at a steady pH. The treatment may be performed by dipping or immersing the pieces in the solution or by directing a flow of solution in close contact over the pieces of material.

After conclusion of this main step in the treatment, the material is treated with a saline solution at an appropriate pH with amine, so as to free the pieces of reactive groups and when necessary to induce desired surface properties to the graft. This latter treatment may also be performed by dipping or immersing the pieces in the solution or directing a flow of solution over the pieces.

The final step consists in additional rinsing of the pieces with a physiological, sterile saline solution or simply with distilled water.

Patches which have undergone the above combined treatment may be supplied in a sterile solution or in dry state. If supply in solution is chosen, the patches are to be removed from the holders and are rolled up with interposition of a dividing foil. The rolled up patches are placed in the sterile solution (which may be one of glutaraldehyde) in an airtight container. Where the dry state is chosen, the pieces are placed in a partly closed container — with or without the holders — are submitted to lyophilization, sterilization, whereupon the container is fully, airtightly sealed.

The accompanying flow sheet (block diagram) illustrates the process set out above and requires no further elucidation.

What is claimed is:

1. A process for diminishing the antigenicity of tissues derived from one species when used as a transplant in a different species, for rendering such tissues substantially resistant to infection, and for rendering such tissues liable to be stored for a prolonged period of time, comprising:
  treating the tissue in a solution of glutaraldehyde in an aqueous solvent of suitable pH; and
  transplanting the treated tissue into an animal species different than that from which the original tissue was derived.

2. The process according to claim 1, wherein said treating step is effected in a 0.3 to 5.0 percent solution of glutaraldehyde.

3. The process according to claim 2, wherein said treating step is effected during 7 to 20 minutes.

4. The process according to claim 1, further including the step of washing the tissue after said treating step and before said transplanting step so as to remove any free glutaraldehyde.

5. The process according to claim 1, further including the step of washing the tissue after said treating step and before said transplanting step with a suitable amino acid, amine or other nucleophile to block any free functional groups of the bound glutaraldehyde.

6. The process according to claim 5, wherein said suitable amino acid, amine or other nucleophile is a suitable amine.

7. The process according to claim 1, further including the step of treating the tissue, after treatment with glutaraldehyde and before said transplanting step, with an agent adapted to modify the surface properties of the tissue.

8. The process according to claim 7, wherein said agent is adapted to attach negative or positive charges to the surface of the tissue.

9. The process according to claim 7, wherein said agent is adapted to attach hydrophobic moieties to the surface of the tissue.

10. The process according to claim 1, wherein the tissue used is skin and said transplanting step is a skin graft.

11. The process according to claim 1, wherein the tissue is a blood vessel.

12. A process according to claim 1, wherein the treated tissue is transplanted into a human and was derived from an animal species other than a human.

13. A process according to claim 1, wherein the treated tissue is pig skin, and said transplanting step is a skin graft.

14. A process for diminishing the antigenicity of tissues intended for use as transplants, for rendering such tissues substantially resistant to infection, and for rendering such tissues liable to be stored for prolonged periods of time, comprising:
  treating the tissue in a solution of glutaraldehyde in an aqueous solvent of suitable pH; and
  transplanting the treated tissue into a human patient.

15. A process according to claim 14, wherein the tissue is derived from a human.

16. The process according to claim 15, wherein the tissue is an amniotic membrane of a newborn.

17. A process according to claim 14, wherein the tissue is derived from an animal species other than human.

18. A process according to claim 17, wherein the tissue is pig skin, and said transplanting step is a skin graft.

19. A process according to claim 14, further including, after said glutaraldehyde treating step and prior to said transplanting step, the step of:
  treating the glutaraldehyde treated tissue with an aqueous solution including glutamic acid.

20. A process according to claim 19, wherein the tissue is a blood vessel.

21. A process according to claim 20, wherein said transplanting step comprises transplanting said treated blood vessel as a substitute for a damaged blood vessel in the human patient.

22. A process according to claim 7, wherein said agent is glutamic acid.

23. A process according to claim 1, wherein said suitable pH is from about 4 to 12.

24. A process according to claim 1, further including, after said glutaraldehyde treating step and prior to said transplanting step, the step of:
  storing the glutaraldehyde treated tissue in a transplant bank for prolonged periods of time.

25. A process according to claim 14, further including, after said gluaraldehyde treating step and prior to said transplanting step, the step of:
  storing the glutaraldehyde treated tissue in a transplant bank for prolonged periods of time.

* * * * *